(12) United States Patent
Platt et al.

(10) Patent No.: US 7,105,110 B2
(45) Date of Patent: *Sep. 12, 2006

(54) DELIVERY SYSTEM FOR POST-OPERATIVE POWER ADJUSTMENT OF ADJUSTABLE LENS

(75) Inventors: Ben C. Platt, Stevenson Ranch, CA (US); Christian A. Sandstedt, Pasadena, CA (US); James A. Ebel, Glendale, CA (US)

(73) Assignee: Calhoun Vision, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/114,861

(22) Filed: Apr. 25, 2005

(65) Prior Publication Data

US 2005/0192563 A1 Sep. 1, 2005

Related U.S. Application Data

(63) Continuation of application No. 09/964,786, filed on Sep. 26, 2001, now Pat. No. 6,905,641.

(60) Provisional application No. 60/269,151, filed on Feb. 15, 2001, provisional application No. 60/235,454, filed on Sep. 26, 2000, provisional application No. 60/235,457, filed on Sep. 26, 2000.

(51) Int. Cl.
*B29D 11/00* (2006.01)

(52) U.S. Cl. ............... 264/1.38; 264/40.1; 264/409

(58) Field of Classification Search ............... 264/1.36, 264/1.38, 408, 409, 40.1; 607/141; 359/642, 359/656; 606/6
See application file for complete search history.

(56) References Cited

U.S. PATENT DOCUMENTS

| | | | |
|---|---|---|---|
| 4,639,100 A * | 1/1987 | Arnaud | ............... 264/1.1 |
| 5,229,797 A | 7/1993 | Futhey et al. | |
| 5,258,024 A | 11/1993 | Chavel et al. | |
| 5,638,212 A * | 6/1997 | Meyers et al. | ............... 359/569 |
| 5,684,636 A | 11/1997 | Chow et al. | |
| 5,777,719 A | 7/1998 | Williams et al. | |
| 5,998,096 A | 12/1999 | Umemoto et al. | |
| 6,086,204 A | 7/2000 | Magnante | |
| 6,139,147 A | 10/2000 | Zhang | |
| 6,476,983 B1 * | 11/2002 | Kodama et al. | ............ 359/795 |
| 6,530,917 B1 | 3/2003 | Seiler et al. | |
| 2003/0048411 A1 | 3/2003 | Jethmalani et al. | |

FOREIGN PATENT DOCUMENTS

EP    0 331 082    9/1989

(Continued)

OTHER PUBLICATIONS

K. Lucke, et al., "A Method of lens extraction for the injection of liquid intraocular lenses," German Journal of Opthamology, 1992 vol. 1, No. 5., pp. 342-345.**

(Continued)

*Primary Examiner*—Chris Fiorilla
*Assistant Examiner*—Yewebdar Tadesse
(74) *Attorney, Agent, or Firm*—Fulbright & Jaworski LLP (57) ABSTRACT

A method and instrument to irradiate a light adjustable lens, for example, inside a human eye, with an appropriate amount of radiation in an appropriate pattern by measuring aberrations in the system containing the lens; aligning a source of the modifying radiation so as to impinge the radiation onto the lens in a pattern that corresponds to the aberration; and controlling the quantity of the impinging radiation whereby to decrease the aberration. The quantity of the impinging radiation is controlled by controlling the intensity and duration of the irradiation. The pattern is controlled and monitored while the lens is irradiated.

28 Claims, 8 Drawing Sheets

FOREIGN PATENT DOCUMENTS

| WO | PCT/US00/41650 | 7/2000 |
|----|----------------|--------|
| WO | WO 00/41650    | 7/2000 |
| WO | WO 00/45759    | 8/2000 |
| WO | WO 01/37031    | 5/2001 |

OTHER PUBLICATIONS

Liang, Junzhong, et al., "Objective measurement of wave aberrations of the human eye with the use of a Hartmann-Shack wavefront sensor," Optical Society of America, vol. 11, No. 7, p. 1949-1957, (Jul. 1994).**

Brandser, Rennaug, et al., "Accuracy of IOL calculation in cataract surgery," Opthalmological Journal of the Nordic Countries, vol. 75, No. 2., p. 162-165, (Apr. 1997).**

Liang, Junzhong, et al., "Aberrations and retinal image quality of the normal human eye," J. Opt. Soc. Am. A. vol. 14, No. II, p. 2873-2882, (Nov. 1997).**

Liang, Junzhong, et al., "Supernormal vision and high-resolution retinal imaging through adaptive optics," Optical Society of America, vol. 14, No. 11, p. 2884-2891, (Nov. 1997).**

Oshika, Tetsuro, et al. "Three year prospective, randomized evaluation of intraocular lens implantation through 3.2 and 5.5 mm incisions," J. Cataract Refract Surg., vol. 24, p. 509-514, (Apr. 1998).**

He, J.C., et al., "Measurement of the wave-front aberration of the eye by a fast psychophysical procedure," Optical Society of America, vol. 15, No. 9, p. 2449-2456, (Sep. 1998).**

Salmon, Thomas O., et al., "Comparison of the eye's wave-front aberration measured psychophysically and with the Shack-Hartmann wave-front sensor," Optical Society of America, vol. 15, No. 9, p. 2457-2465, (Sep. 1998).**

Charters, Lynda, "New IOL lets laser adjust refraction postimplantation," Hotel & Motel Management, Opthamology Times, (Jul. 1, 2000).**

Mahoney, Robert K., et al. "Laser Adjustable Lens: a new generation in implants," Ocular Surgery News, vol. 18, No. 15, (Aug. 1, 2000).**

Bethke, Walter, "An IOL You Can Customize," Review of Opthamology, (Sep. 2000).**

Roos, et al., Photonics Spectra, Circle 77 (2001). **

International Search Report issued for PCT/US01/30300, dated Mar. 13, 2002.

Partial European Search Report issued for EP 01 97 5499, dated Apr. 11, 2005.**

* cited by examiner

FIG. 8
SPECTRAL OUTPUT OF UV LED

DELIVERY SYSTEM FOR POST-OPERATIVE POWER ADJUSTMENT OF ADJUSTABLE LENS

CROSS REFERENCE TO RELATED APPLICATIONS

This application is a continuation of Ser. No. 09/964,786, filed on Sep. 26,2001, now U.S. Pat. No. 6,905,641, is based on U.S. application Ser. No. 60/235,457, filed Sep. 26, 2000; Ser. No. 60/235,454 filed Sep. 26, 2000; and Ser. No. 60/269,151, filed Feb. 15, 2001, and Ser. No. 09/964,786, filed Sep. 26, 2001.

BACKGROUND OF THE INVENTION

1. Field of the Invention

This invention relates generally to the post-manufacture alteration of the properties of an optical device, and, more specifically, to the irradiation of light adjustable lenses.

2. Background Information

Cataract surgery procedures involve making an incision in the anterior lens capsule to remove the cataractous crystalline lens and implanting an intraocular lens (IOL) in its place. In general, there are two types of intraocular lenses. One type replaces the eye's natural lens, usually to replace a cataractous lens. The other type is used to supplement an existing lens and functions as a permanent corrective lens. This type of lens (referred to as a phakic IOL) is implanted in the anterior or posterior chamber to correct refractive errors of the eye. In theory, the power for either type of IOL required for enmetropia (i.e., point focus on the retina from light originating at infinity) can be precisely calculated. The power of the implanted lens is selected based on pre-operative measurements of ocular length and corneal curvature to enable the patient to see without additional corrective measures (e.g., glasses or contact lenses). Unfortunately, due to errors in measurement, and/or variable lens positioning and wound hearing, about half of these patients undergoing this procedure will not enjoy optimal vision without correction after surgery (Brandser et al., *Acta Opthalmol Scand* 75:162–165 (1997); Oshika et al., *J Cataract Refract Surg* 24:509–514 (1998). Because the power of such IOLs generally cannot be adjusted once they have been implanted, the patient typically must be resigned to the use of additional corrective lenses such as eye glasses or contact lenses. Rarely is the implanted lens exchanged for one of more appropriate lens power.

An answer to the foregoing problems is a light adjustable lens, which is an optical device whose refraction properties can be changed after its fabrication and insertion into a human eye. Such a lens is described in detail in International Application Ser. No. PCT/US99/23728, filed on Oct. 13, 1999 and published Jul. 20, 2000, the disclosure of which is incorporated herein by this reference. The light adjustable lens has a refraction modulating composition dispersed in a polymer matrix. One to four weeks after the lens has been implanted into the eye and refractive stabilization has occurred, the preexisting optical aberrations or those induced by the surgical procedure are measured. In order to correct these optical aberations (e.g., spherical power, astigmatism, prism, etc.) a corresponding amount of radiation is applied to the light adjustable lens which alters the optical properties of the lens, through changes in its shape, its index of refraction, or both. Following one or several irradiations in which portions of the lens have been exposed to selectively and spatially modify the refractive power the entire lens is irradiated to "lock in" the modified lens power.

The irradiation sources that have enough intensity to modify the refractive properties of an implanted, adjustable intraocular lens in situ are either coherent light sources such as a laser, which can potentially cause permanent damage to the retina by creating high intensities focused to a point on the retina, or high power incoherent sources that have to be attenuated by as much as $1/1000$ in order to avoid damage to the eye. Accordingly, there is a need for an irradiation source to modify an intraocular lens, e.g., in situ after implantation of the lens in the eye.

There is also a need to more accurately modify the lens so as to more closely compensate for remaining aberrations, and a need to assure that locking radiation will irradiate the lens behind the iris in patients where the iris does not fully dilate.

SUMMARY OF THE INVENTION

The present invention provides a method and instrument to irradiate a light adjustable lens (LAL) inside the human eye with an appropriate amount of radiation in an appropriate pattern. A similar embodiment of the design described here can also be used to irradiate light adjustable lens material for other applications. For example, the invention can be used as an aberration conjugator in correcting other types of optical systems, e.g., microscopes, telescopes, camera lenses, and the like. By accurately irradiating the light adjustable lens to correct the patients' vision after implantation, the patient does not have to wear eye glasses after surgery (this is not strictly correct. Our lens in its current form does not allow for accommodation. Thus, older patients who have lost the ability to accommodate would have to wear some sort of corrective eyewear. The key is that for driving and performing most other functions they would not have to wear glasses or contact lenses). In accordance with embodiments of this invention, following implantation, aberrations in the eye are measured before, during, and after irradiation, the radiation source is precisely aligned to the light adjustable lens inside the eye, the intensity and duration of the irradiation are precisely controlled, and the irradiation pattern is controlled and monitored. There is provided a method and instrument that is easy for doctors to use, and which is patient friendly.

Various forms of correction may be required, such as spherical power, astigmatism, and higher order aberrations (e.g., coma, trefoil, third order spherical, etc.). Different amounts and patterns of irradiation will be required to correct the patients' vision. Thus, in a method and instrument for irradiating a light adjustable lens in an optical system with lens modifying radiation, the present invention provides an improvement comprising: measuring aberrations in the optical system (e.g., the eye) containing the lens (including preexisting aberrations and those induced by the surgical procedure and wound healing); aligning the source of the modifying radiation so as to impinge the irradiation onto the lens in a spatially defined intensity pattern that will null be aberration. The quantity of the impinging radiation is controlled by controlling the intensity and duration of the irradiation. The pattern is controlled and monitored while the lens is irradiated.

Specific embodiments of the invention provide energy sources for irradiating light adjustable intraocular lenses. In one embodiment of the invention, an extended ultraviolet light (UV) source is provided, e.g., UV light emitting diodes (LED) for irradiating the lens. UV LEDs are extended, low intensity light sources. In a more specific embodiment, four to eight UV LEDs are fed into the end of a light pipe, e.g., coupled into a five mm diameter optical fiber, to create an energy source for light adjustable lens irradiation.

Other useful sources of UV for modifying the light adjustable lens are: pulsed UV laser, such as obtained with a flash-lamp laser; and continuous wave (CW) UV, such as obtained from an arc lamp, CW laser or CW LED.

In accordance with another embodiment of the invention, modifying light is generated and projected onto the light adjustable lens in a pattern that compensates for the aberration, for example, one that is opposite in phase to the measured aberrations. In a particular form of this embodiment, a UV vertical-cavity surface-emitting laser (VCSEL) array is used to generate a UV intensity pattern and project it onto the surface of a light adjustable lens. Such an arrangement provides advantages in that the optical system is smaller, lighter, and less complicated than other UV patterning systems. The optical efficiency is higher than other systems, producing less heat; and the operating lifetime of the source is longer.

In another embodiment of the invention, the pattern of modifying light is obtained by use of an apodizing filter having a predetermined intensity profile. In still other embodiments, a spatial light modulator or digital light processor can be used. Such devices have been used in LASIX procedures to modify the original lens, but their use in providing a pattern of modifying light for the refraction modulating component of a light adjustable lens is unique. In any event, the pattern of light can be obtained by the use of photo-feedback, for example from a Shack-Hartmann (also referred to as Hartmann-Shack) sensor. Such a sensor has been used to modify the aberrations of an astronomical telescope. Its use to pattern the refractive properties of a light adjustable lens is unique.

Once the light adjustable lens is modified to the desired extent, the properties of the lens are locked in by further, but total, non-patterned radiation. A flooding beam of radiation can be used, having a "top hat" intensity profile, or one can use an intensity profile that diminishes as the radius (r) increases, e.g., by the formula: $(1-r^2)/r^2$. A specific concern in the locking irradiation of a light adjustable intraocular lens is the ability to irradiate the lens behind the iris in patients where the iris does not fully dilate. In accordance with another embodiment of this invention, a gonio lens is used to overcome this problem. The gonio lens was originally developed to view behind or in front of the iris at extremely large angles. It is also used to view portions of the retina that are otherwise obstructed by ocular structure. It's use in the present invention to lock in the refractive modifications of a light adjustable lens is unique.

The foregoing has outlined rather broadly the features and technical advantages of the present invention in order that the detailed description of the invention that follows may be better understood. The foregoing, and additional features and advantages of the invention will be described hereinafter, form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DESCRIPTION OF REPRESENTATIVE EMBODIMENTS

Generally, a light adjustable lens comprises a first polymer matrix and a refraction modulating composition dispersed therein. The first polymer matrix forms the optical element framework and is generally responsible for many of its material properties. The refraction modulating composition may be a single compound or a combination of compounds that is capable of stimulus-induced polymerization, preferably photo-polymerization. As used herein, the term "polymerization" refers to a reaction wherein at least one of the components of the refraction modulating composition reacts to form at least one covalent or physical bond with either a like component or with a different component. The identities of the first polymer matrix and the refraction modulating compositions will depend on the end use of the optical element. However, as a general rule, the first polymer matrix and the refraction modulating composition are selected such that the components that comprise the refraction modulating composition are capable of diffusion within the first polymer matrix. Put another way, a loose first polymer matrix will tend to be paired with larger refraction modulating composition components and a tight first polymer matrix will tend to be paired with smaller refraction modulating composition components.

Figure 1:
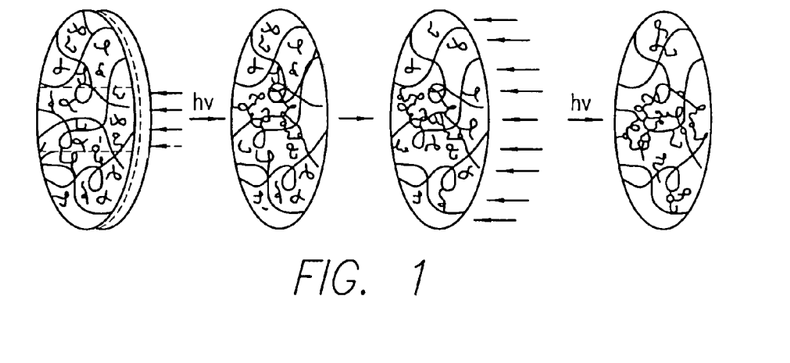
FIG. 1 is a schematic depiction of a lens of the present invention being irradiated in the center followed by irradiation of the entire lens to lock in the modified power.

Upon exposure to an appropriate energy source (e.g., heat or light), the refraction modulating composition typically forms a second polymer matrix in the exposed region of the optical element. The presence of the second polymer matrix changes the material characteristics of this portion of the optical element to modulate its refraction capabilities. In general, the formation of the second polymer matrix typically increases the refractive index of the affected portion of the optical element and also changes its shape. After exposure, the refraction modulating composition in the unexposed region will migrate into the exposed region over time causing a swelling reaction or shape change. The amount of refraction modulating composition migration into the exposed region is time dependent and may be precisely controlled. If enough time is permitted, the refraction modulating composition components will re-equilibrate and redistribute throughout optical element (i.e., the first polymer matrix, including the exposed region). When the region is re-exposed to the energy source, the refraction modulating composition that has since migrated into the region (which may be less than if the refraction modulating composition were allowed to re-equilibrate) polymerizes to further increase the formation of the second polymer matrix. This process (exposure followed by an appropriate time interval to allow for diffusion) may be repeated until the exposed region of the optical element has reached the desired property (e.g., power, refractive index, or shape). At this point, the entire optical element is exposed to the energy source to "lock-in" the desired lens property by polymerizing the remaining refraction modulating composition components that are outside the exposed region before the components can migrate into the exposed region. In other words, because freely diffusable refraction modulating composition components are no longer available, subsequent exposure of the optical element to an energy source cannot further change its power. FIG. 1, taken from International Application Ser. No. PCT/US99/23728, supra, illustrates refraction modulation (thus lens power modulation) followed by a lock in.

The irradiation system of the exemplary embodiments consist of several major parts, 1) radiation source, 2) beam shaper, 3) beam delivery system, 4) method of alignment, 5) calibration element, and 6) diagnostic element, and 7) locking element. Each will be described in more detail below.

Radiation Source

The radiation source must be compatible with the sensitivity of the material being irradiated. In this example, the photopolymer is sensitive to UV radiation between the wavelengths of 325 nm and 380 nm so the irradiation source is a UV source. The UV source can be a laser, light emitting diode, or various types of lamps that have a UV spectrum. The source can also be continuous (CW) or pulsed. The source in this example is a CW mercury arc lamp with a filter at 365 nm+/−10 nm. Other methods appropriate for use in the present system are described more fully below under the heading: "Method for Irradiating Adjustable Implantable Lenses."

Beam Shaper

The nature of the beam shaper will depend on the type of radiation used, such as, e-beam, microwave, radio frequency, acoustic, or optical. Optical lenses and mask will be used in this example since the radiation source is an arc lamp. The present methods allow a customized pattern of irradiation to generate a customized refraction change in the light adjustable lens. The optical mask (or pattern generator) can be generated using several methods, such as, a photographic film (or any other type of film) pattern (continuous tone or halftone), a liquid crystal display, a digital mirror device, rotating or translating patterns, or any other method to vary the intensity profile or integration time of the exposed radiation. Some lasers are naturally apodized and may not require further intensity modulation for correcting power or astigmatism in a light adjustable lens. In one embodiment, a photographic film mask is used. A photographic film is placed between two glass slides to produce the 2-D intensity profile in a UV projection system, similar to a conventional slide projection, using a UV source, condenser optics, field lens, film mask (or pattern generator), and projection optics. Methods for generating irradiation profiles are described more fully below under the heading: "Methods for Generating Irradiation Intensity Profiles."

Another source is a UV vertical cavity surface-emitting laser (VCSEL). In contrast to the use of photographic film, described above, with a VCSEL array, one only needs a laser array, lens matrix array, and projection optics. Thus, the advantages are lower cost and complexity. A controlled VCSEL 2-D array of lasers replaces a mask or SLM, and the light source with its associated condenser optics to irradiate light adjustable lenses or films. The use of a UV vertical cavity surface-emitting laser (VCSEL) constitutes an embodiment of this invention and is described more fully below under the heading "UV-VCSEL UV Pattern Generator."

Beam Delivery System

The beam delivery system will depend on the type of beam being delivered. In this example, a UV beam is being delivered so UV optics will be used. The objective lens images the mask (intensity pattern) onto the light adjustable lens. The condensor lens, which images the output of the integrator onto the mask, is imaged onto the objective lens with a field lens. This design is referred to as critical illumination. Another form of illumination is called Kohler illumination, where the source is imaged onto the objective lens and there is not field lens. This type of illumination system is used if a beam integrator is not used. Either type of illumination design can be used.

Alignment System

Figure 2:
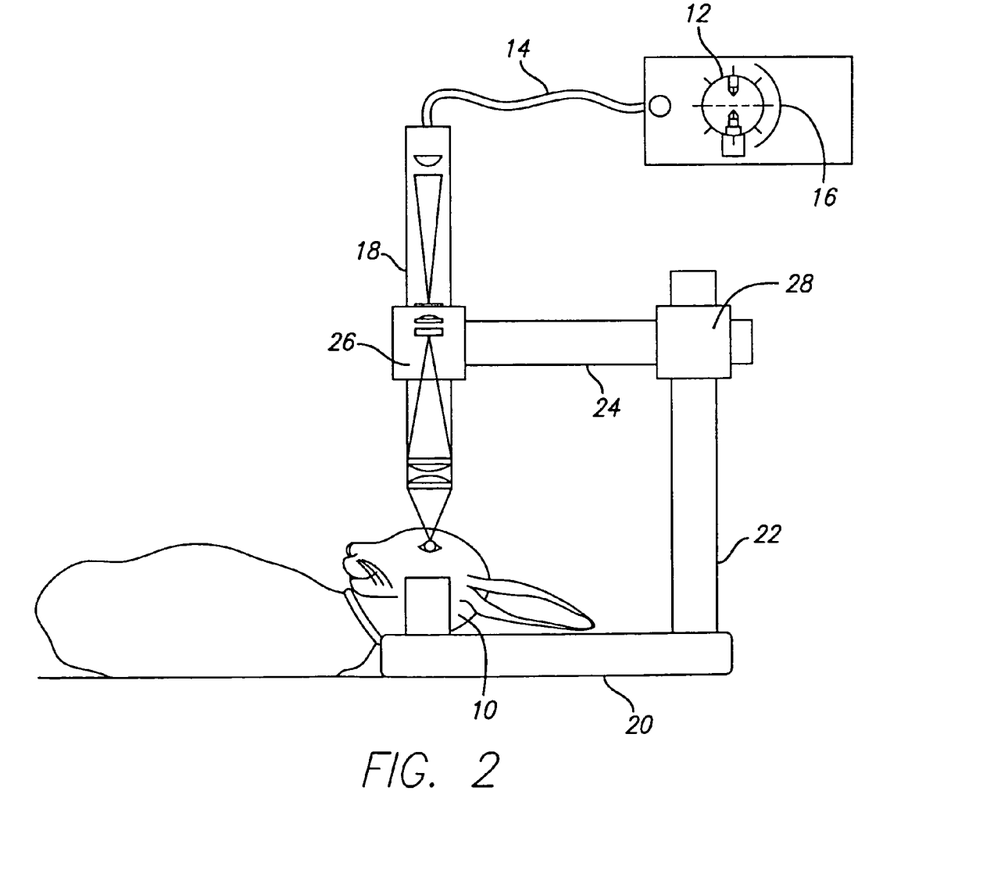
FIG. 2 schematic depiction of an example of an irradiation system without an internal alignment element.

An example of an irradiation system without an internal alignment element is shown in FIG. 2 as used on the eye of a rabbit 10. The arc lamp is focused onto the input of an integrator, in this case an optical fiber in the form of a hollow liquid filled waveguide referred to in the drawing as a source fiber 12. The output of the integrator is uniform. It is focused onto an optical mask generator contained in a tube 14 to produce the desired irradiation pattern. In this illustration, the rabbit's head is secured to a platform 16 having a stand 18. The optics tube 14 is connected an arm 20 by means of a fine adjustment clamp 22, the arm 20 extending from and secured to the stand 18 by a coarse adjustment clamp 24. The desired irradiation/mask pattern will depend on the desired refractive change in the light adjustable lens and the interaction of the material with the radiation. This relationship will be a mathematical description that we refer to as a nomogram.

Figure 3:
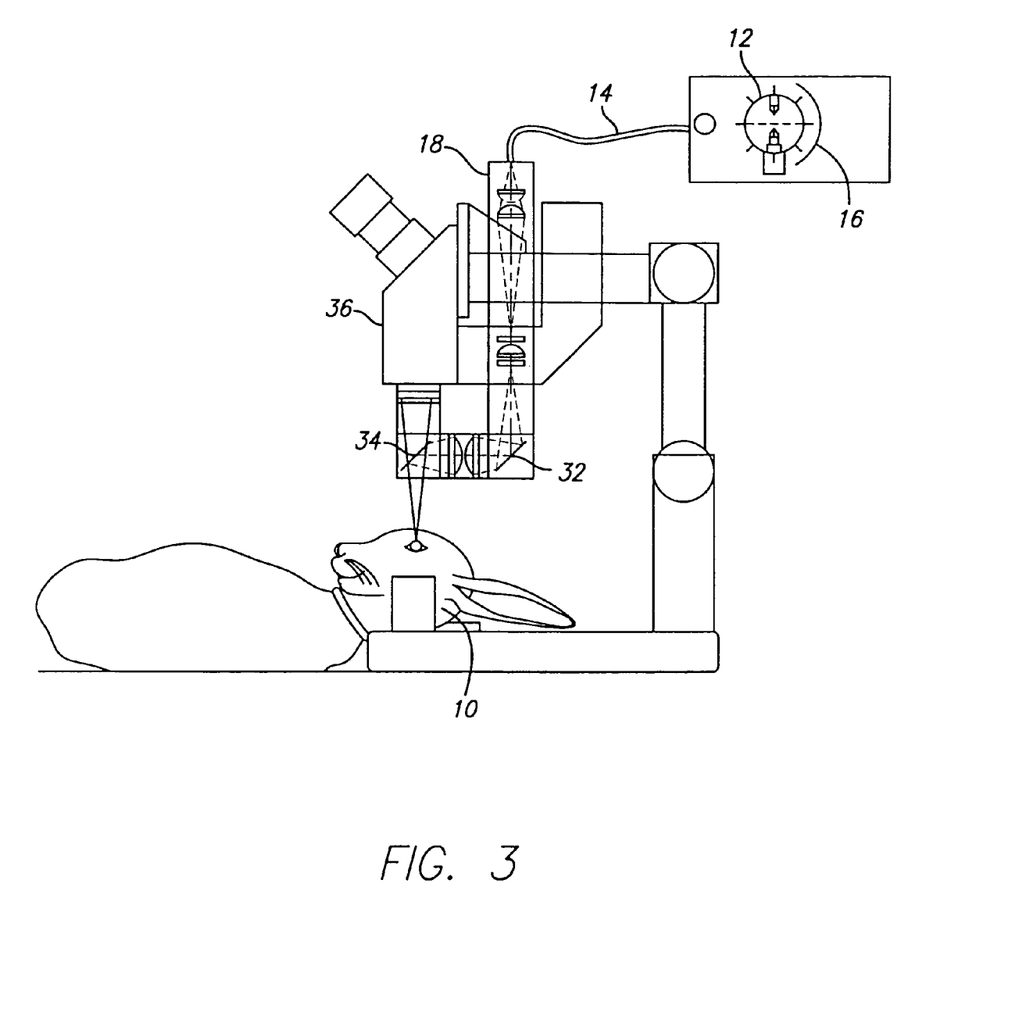
FIG. 3 schematic depiction of an example of irradiation system in a surgical microscope configuration.

The method of alignment includes accurate placement of the irradiation pattern on the light adjustable lens. In this case the light adjustable lens is an intraocular lens implanted in the patient's eye. The two most likely positions of the human patient or other subject is lying down on a table, as shown by the reclining rabbit 12 in FIG. 3, or sitting in a chair, as shown by the human patient 26 FIG. 4. Referring to FIG. 3, UV light from the source fiber 12 directed through the optical mask generator tube 14 is diverted by a mirror 28 to a beam splitter 30 and from there to the rabbit's eye. The beam splitter 30 permits observation of the rabbit's eye and of the procedure through a surgical microscope 32 vertically aligned with the beamsplitter 30.

Figure 4:
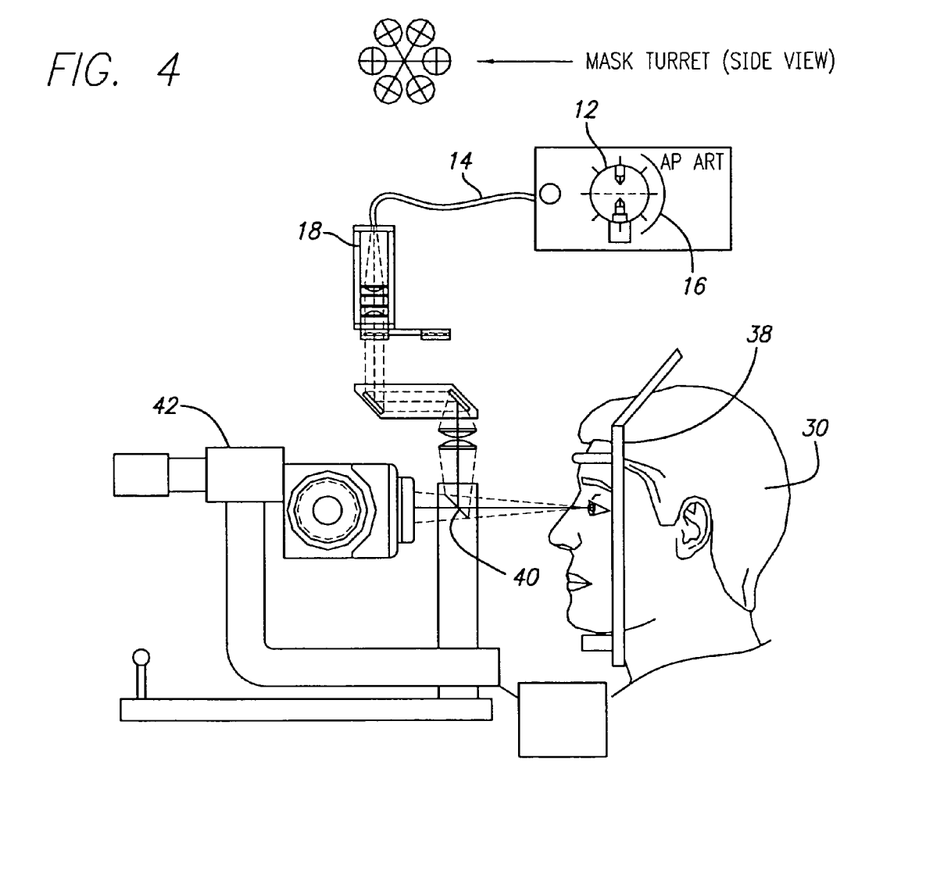
FIG. 4 schematic depiction of an example of an irradiation system in a slit lamp configuration.

Referring to FIG. 4, If the patient is setting in a chair, his or her head is placed on a headrest 34 that supports the chin and forehead. UV light from the source fiber 12 directed through the optical mask generator tube 14 is diverted by a beam splitter 36 and from there to the patient's eye. The beam splitter 36 operated in conjunction with an ophthalmic slit lamp 38 that has its own observation optics (not shown) and which allows makes a good system for aligning the irradiation source to the patient.

The slit lamp can have any of a number of configurations, including, hand held, portable, and table mounted. All are applicable to a certain extent. If the patient is lying on a table, a configuration similar to the surgical microscope 32 of FIG. 3 is a good setup.

Once the head is held stable, a video camera or visual microscope co-aligned and parafocal with the optical axis of the irradiation source, is used to align the projected mask/intensity pattern to the light adjustable lens. Internal or external light sources reflecting off the cornea or light adjustable lens can be used as angular alignment aids to align the irradiation source to the light adjustable lens. The reflections may be visible with the video camera, the visual microscope, or another sensor.

Eye tracking and beam control may not be necessary for short exposures and low spatial frequency intensity profile pattern. For long exposures and high spatial frequency intensity patterns, eye tracking will be necessary and the beam will either have to be shuttered when the beam goes out of alignment or controlled to follow the eye motion.

Calibration Element

A calibration element is a sensor that monitors the power and/or the intensity profile of the irradiation beam. A beamsplitter is used to provide a sample of the beam for measurement. For simple aberrations, such as optical power or astigmatism, the intensity profile may be fixed with a given mask/pattern generator and it will only be necessary to measure the total power and time of exposure. For customized intensity profiles, it will be necessary to monitor the projected intensity profile and time of exposure. For UV radiation, a UV CCD camera can be used to monitor the intensity.

Figure 5:
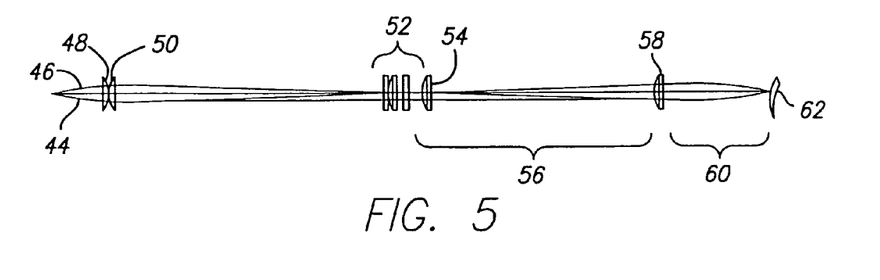
FIG. 5 is a schematic depiction of an example of optical design for imaging through a mask onto light adjustable lens.

An example of the optics in the tube 14 of FIGS. 2 to 4 for imaging the mask onto the light adjustable lens is the illumination optical design of FIG. 5. UV light 40 from a source 42, e.g., a liquid filled optical wave guide, is directed through silica optics composed of a PLCX-25.4-38.6-UV lens 44 spaced 1 mm from a PLCX-25.4-30.9-UV lens 46 which is separated, 215 mm in this example, from a compound PLCX-25.4-46.4-UV lens set 48. The UV light 40 passes through a mask 50, then after a variable space 52 through a lightpath gradium CPX-25-60 lens 54, to the light adjustable lens 56 over a variable space 58.

Diagnostic Element

The diagnostic element described here is used to measure the aberrations in the light adjustable lens before, during, and/or after irradiation. There are many instruments available to measure aberrations in the eye. The same instruments used to determine a patient's prescription for eye glasses can be used to measure optical power and astigmatism errors in the light adjustable lens. There are also several instruments for measuring higher order aberrations in the light adjustable lens. The three most common sensors used today are based on the Schemer disk, the Shack Hartmann wavefront sensor, and the Talbot interferometer. The application of a wavefront sensor to a light adjustable lens is discussed more fully below under the heading: "Application of Wavefront Sensor to Lenses Capable of Post-Fabrication Power Modification". The diagnostic instrument can be a stand-alone instrument or it can be built into the irradiation system. The diagnostics can be performed during irradiation more readily when the diagnostics are built into the irradiation system.

In a particular implementation: a) a Shack Hartmann wavefront sensor is used to measure the aberrations in the eye; b) nomogram equations are used to calculate the required intensity profile to correct the measured aberrations; c) the required intensity profile is placed on a programmable mask generator (such as a digital mirror device); d) a calibration camera is used in a closed loop operation to correct the digital mirror device to compensate for aberrations in the projection optics and non-uniformity in the light source; e) the light adjustable lens is radiated for the prescribed time period; and f) after a specified time, the aberrations in the eye are re-measured to ensure that the proper correction was made. If necessary, the process is repeated until the correction is within limits.

Figure 6:
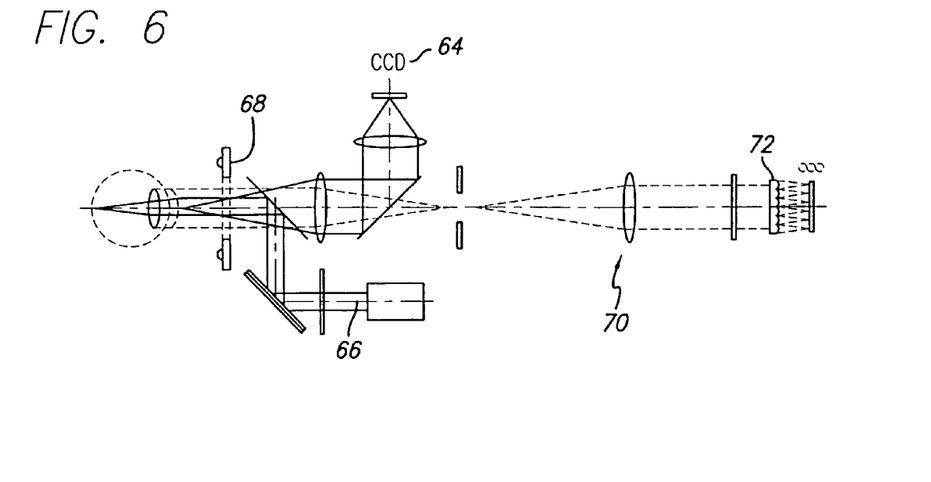
FIG. 6 is a schematic depiction of an embodiment of the Shack-Hartmann wavefront sensor.
Figure 7A:
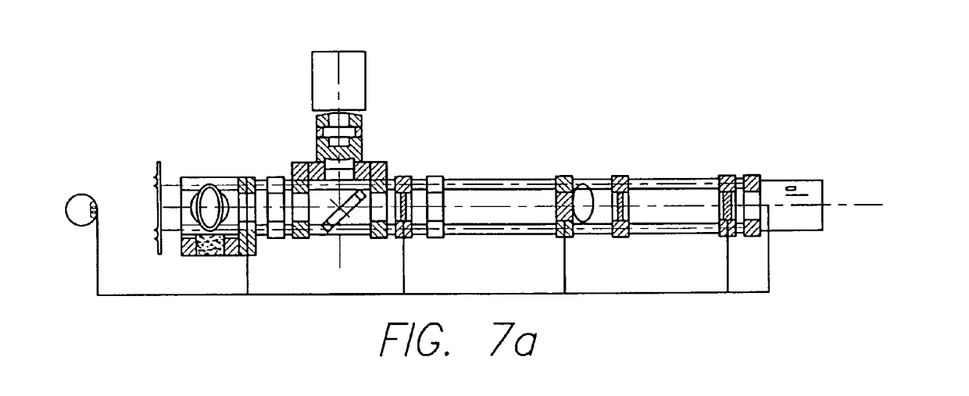
FIGS. 7a and 7b are, respectively, schematic depictions of a side and top view of a Shack-Hartmann wavefront sensor.
Figure 7B:
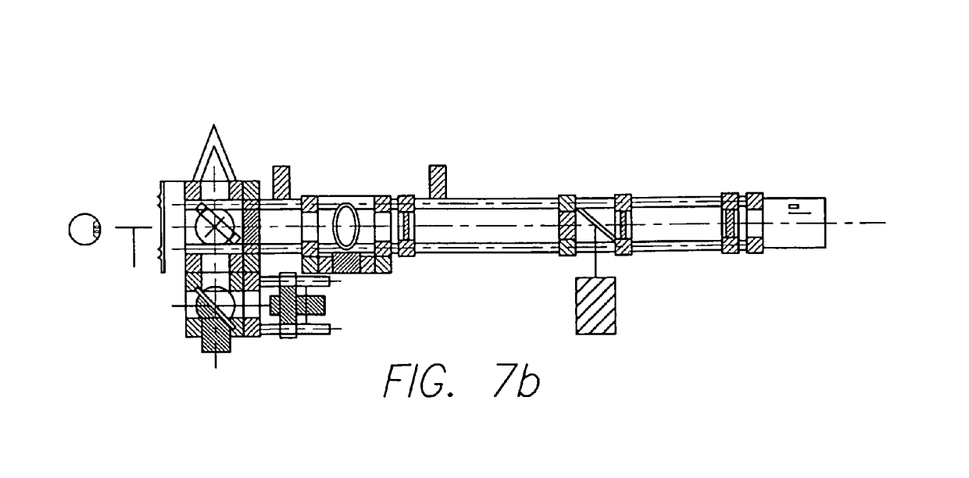

An exemplary embodiment using a Shack-Hartmann wavefront sensor is shown schematically in FIG. 6. Additional detail for the wavefront sensor is shown in the side and top views of FIGS. 7a and 8b. This pair of figures gives some of the dimensions for this exemplary embodiment as shown from the side and top the Shack-Hartmann wavefront sensor.

In the view shown in FIG. 6, for convenience of illustration, the CCD imaging path is drawn to the side of the system. In reality, the CCD is mounted on top of the system. The collimated laser beam, wavelength 780 nm (barely visible) is focused on the retina at a diameter of about 2 mm. The CCD camera provides the surgeon with a b/w image of the eye. This is useful for centering the eye. The image can be focused by moving the sensor back and forth relative to the eye. This ensures that the patient's eye is located at the correct distance from the sensor. The laser light is reflected and scattered from the retina and exits the eye. The exiting wavefront contains the aberrations of the eye. The telescope with aperture stop works as a spatial filter, the short wave pass filter blocking the reflected 880 nm light of the illumination LEDs.

An array of microscopic lenses form the heart of the Shack-Hartmann sensor. This lenslet array dissects the incoming light into a large number of sub-apertures, and then measures the wavefront slope across each subaperture. The sensor information is used to analyze the optical properties of the system which created the wavefront (in this case, the eye). Starting at the retina, an ideal wavefront is generated which passes through the optical path of the eye. As the wavefront exits the eye, it contains a complete map of the eye's aberration for analysis by the sensor. Once the wavefront is received by the sensor, a complex series of analyses are performed to provide a "complete" picture of the eye's optical path. This information may then be visualized and reported in a number of formats including wavefront error and Zernike polynomials. Zernike polynomials have been in use since 1934 to mathematically describe the aberrations in an optical system. The benefit of this analysis is that the wavefront can be broken into independent components which represent specific aberrations. The severity of each of these components may then be analyzed and corrected through the techniques of this invention.

Locking Element

Once the aberrations are corrected, locking irradiation is applied. The locking irradiation may or may not be applied with the same irradiation system. In those cases where the iris does not fully dilate, it may be necessary to irradiate the light adjustable lens behind the iris. In accordance with another embodiment of the invention a gonio lens is used for this purpose as will be more fully described below under the heading "Gonio Lens to Lock Light Adjustable Lens."

The following will provide additional detail of various embodiments.

Method for Irradiating Adjustable Implantable Lenses

One form of energy used to irradiate an optical element e.g., a light adjustable lens is UV irradiation. For example, a Helium Cadmium (HeCd) laser operating at 325 nm and a mercury (Hg) arc lamp with spectral lines at 333 and 365 nm. have been used in this invention, All of these UV sources, including the tripled frequency laser diode pumped solid stated laser operating at 355 nm and broad band xenon lamps operating with any narrow band spectral filter, are useful sources for conducting UV irradiation tests on light adjustable lens light adjustable lens materials and test light adjustable lens.

There are potential safety issues related to each of these sources. When using a laser, there is the potential that the source can be focused to a point on the retina, creating high intensities that can cause permanent damage. The other lamp sources all start out at high power levels that have to be attenuated by as much as $1/1000$. A typical 100 watt Hg. arc lamp coupled to a liquid filled optical fiber can melt a plastic ruler if the attenuator is accidentally omitted.

A safer source would be one that cannot be focused to a point and has only enough power to expose/irradiate the intraocular lens material. In accordance with an embodiment of the invention, 0.6 to 0.8 milliwatts (mW) of total UV power, in the 350 to 380 nm spectral band, incident on the light adjustable lens are used, and are sufficient to create the desired swelling or power change. With optical and corneal transmission losses, the total required power in the UV source will be approximately 2.5 to 3.5 mW.

Figure 8:
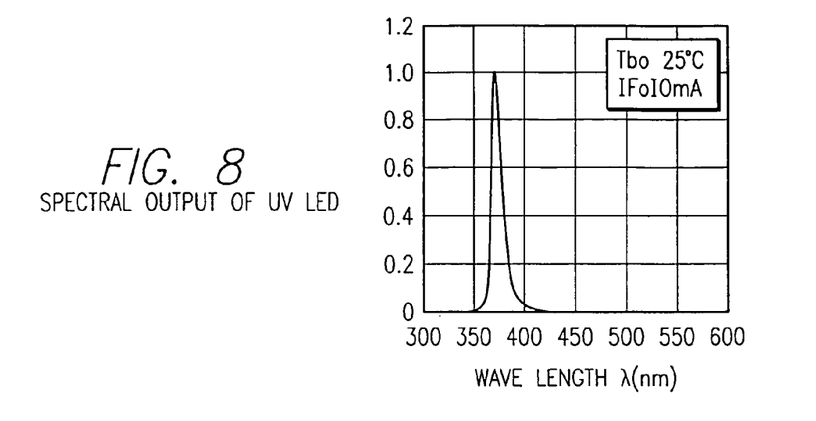
FIG. 8 illustrates a spectral output of a UV Light Emitting Diode.
Figure 9A:
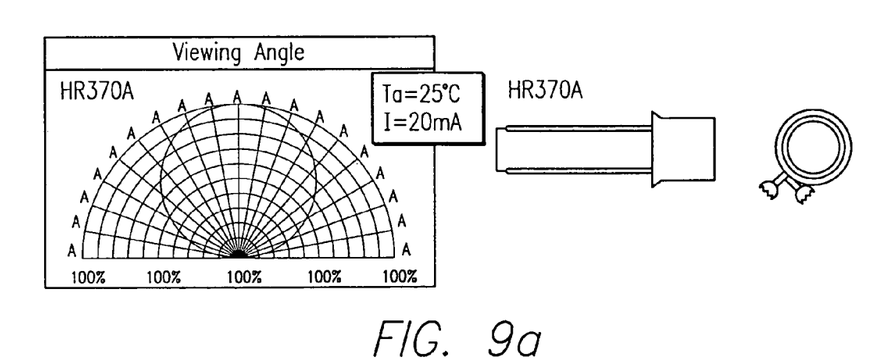
FIGS. 9a and 9b show mechanical descriptions and irradiation patterns of a UV Light Emitting Diode.
Figure 9B:
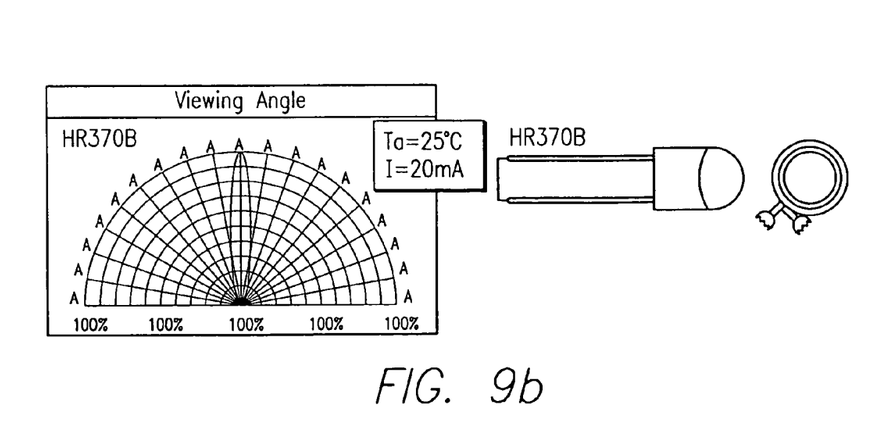

In accordance with the present invention, a UV LED can be a suitable energy source for irradiation of light adjustable lens. For example, one can use a UV LED available on the market that has an optical output power of 0.75 to 1 mW centered at 370 nm with a full width half max spectral bandwidth of —10 nm. The radiation coming out of the LED module spreads over a 100 degree cone without the ball lens and over a 10 degree cone with the ball lens. The commercially available UV LED is an extended source and it can be focused to a small enough size to couple into a liquid filled optical fiber. The spectral output is shown in FIG. 8. A description of the mechanical package and radiation profiles from the UV LEDs is shown in FIGS. 9a and 9b. Optical and electrical properties of the UV LED, obtained from a vendor specification sheet (______ ______) are given in Table 1.

TABLE I

| Absolute Maximum Ratings (Ta = 25° C.) | | | | |
|---|---|---|---|---|
| | Symbol | Unit | HR370A | HR370B |
| DC Forward Current | IF | MA | 15 | 15 |
| Pulse Forward Current | IFP | MA | 30 | 30 | 1) |
| Reverse Voltage | VR | V | 5 | 5 |

TABLE I-continued

| Power Dissipation | PD | MW | 45 | 45 |
|---|---|---|---|---|
| Operating temperature | Topt | ° C. | −30 . . . +80 | −30 . . . +80 |
| Storage Temperature | Tstg | ° C. | −40 . . . +100 | −40 . . . +100 |

1) Pulse width max. 10 ms, Duty ratio max. 1/10

| | Symbol | Unit | Condition | Min. | Typ. | Max. |
|---|---|---|---|---|---|---|
| HR370A Electrical Optical Characteristics (Ta = 25° C.) | | | | | | |
| DC Forward Voltage | VF | V | IF = 10 mA | — | 3.9 | — |
| DC Reverse Current | IR | MA | VR = 5 V | — | — | 50 |
| Optical Power Output | PO | MW | IF = 10 mA | — | 1000 | — |
| Peak Wavelength | λ | Nm | IF = 10 mA | — | 370 | — |
| Spectrum Half Width | Δλ | Nm | IF = 10 mA | — | 12 | — |
| HR370B Electrical Optical Characteristics (Ta = 25° C.) | | | | | | |
| DC Forward Voltage | VF | V | IF = 10 mA | — | 3.9 | — |
| DC Reverse Current | IR | MA | VR = 5 V | — | — | 50 |
| Optical Power Output | PO | MW | IF = 10 mA | — | 750 | — |
| Peak Wavelength | λ | Nm | IF = 10 mA | — | 370 | — |
| Spectrum Half Width | Δλ | Nm | IF = 10 mA | — | 12 | — |

In one embodiment, 2 to 10 UV LEDs are coupled into a 5 mm diameter optical fiber. In another embodiment, 4 to 8 UV LEDs are coupled into a 5 mm diameter optical fiber. UV LEDs can be added or subtracted as required to produce a safe and sufficient power level at the cornea. Optics can be designed to image the end of the fiber onto a Digital Light Processor (DLP) chip, or other types of profile generators, and then image the chip onto the light adjustable light adjustable lens. A field lens can be placed near the DLP chip for imaging the fiber optic projection lens onto the light adjustable lens objective lens.

In a particular example, the light adjustable lens is implanted in a patient's eye and the eye's refraction is allowed to stabilize. Aberration analysis is made of the patient's eye using standard refraction techniques and/or a wavefront sensor. This data, along with a previously derived nomogram, is used to calculate the desired irradiation profile and dosage desired to correct the patient's vision by adjusting the light adjustable lens with UV light. The pattern is transferred to the projection system and the eye/light adjustable lens is irradiated using the UV LED as a source.

The UV LED is a suitable safe UV source to use in the irradiation system for modifying the optical properties of light adjustable lens in patients. It has limited brightness and limited size. The maximum possible brightness will be kept below the American National Standards Institute guidelines, and the minimum size of the spot on the light adjustable lens will be the image of the output of the optical fiber.

Methods for Generating Irradiation Intensity Profiles

During exposure to modifying radiation, macromer diffuses into the irradiated volume, producing a concomitant swelling of the lens. The localized swelling changes the local radius of curvature of the lens as previously shown in FIG. 1. In addition, slight changes in the refractive index of the exposed region of the lens will occur since the refractive index is proportional to the number of molecules/volume.

If swelling occurs in the center of the lens, the radius of curvature in the central optical zone gets shorter. If swelling occurs near the edge of the lens, the radius of curvature in the central optical zone gets longer. This swelling is not necessarily a linear function of the irradiation because of boundary conditions at the edge of the lens, non-uniform thickness across the lens, and, possibly, non linear response of the lens material to the irradiation. The irradiation profile, amplitude, and exposure time must be tailored for each patient to produce the correct amount of change in the IOL. This includes IOL power change (diopters), astigmatism, spherical aberrations, and other irregularities. This is referred to as customized irradiation.

According to an embodiment of the present invention, a spatial light modulator can be used to generate customized irradiation intensity profile for a composition comprising a refraction modulating composition dispersed in a polymer matrix forming e.g., an IOL. The spatial light modulator can be any suitable ones known to one skilled in the art. In one embodiment, the spatial light modulator is a liquid crystal display or a digital light processors.

For example, electromagnetic irradiation in the UV, visible, or near infrared portions of the spectrum is easily projected onto the lens by using a projection system similar to the ones used in commercial video/computer projection systems. Nevertheless these projectors use the liquid crystal display or digital light processor to replace the film used in the projectors. Liquid crystal displays can operate in either transmission or reflection mode. Since they rotate the plane of polarization of the light, polarized light and an analyzer must be incorporated into the optical system. Digital light processors are composed of an array of tiny square mirrors typically 17 microns on a side. Rather than modulate the intensity of the beam, they modulate the time the beam is on the screen. The tiny mirrors can tilt +/−10 degrees at a rate of 60 kHz. If the mirror is activated, it reflects the light into the projection lens. If the mirror is not activated, the light reflects to a beam dump and does not make it to the screen. For each of the 60 kHz frames, each mirror is either activated or not. Thus, the mirror activation is binary i.e. on or off. For uniform illumination on the digital light processor, the energy density profile applied to the lens is proportional to the number of times each mirror is activated and not to the intensity of the beam.

The method of using constant incident intensity and spatially varying the exposure time has several advantages: a) it avoids trying to produce exposure levels below the intensity threshold level (the minimum irradiation level that any effect occurs), b) it avoids having to compensate for the material efficiency versus intensity level, and c) it makes the nomograms (a plot detailing an IOLs response to light intensity, profile, and duration) much easier to develop.

Figure 10A:
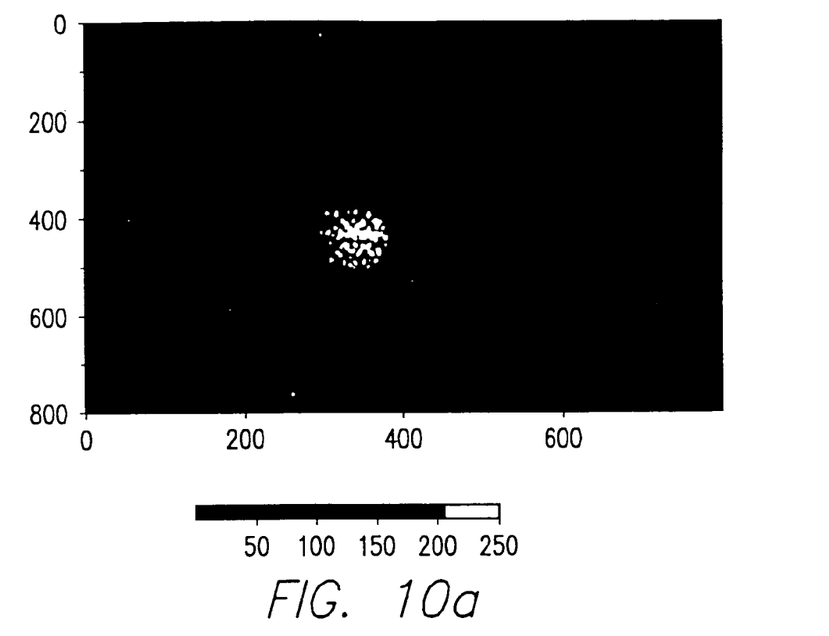
FIGS. 10a and 10b are examples of irradiation profiles for correcting the optical power of a light adjustable lens.
Figure 10B:
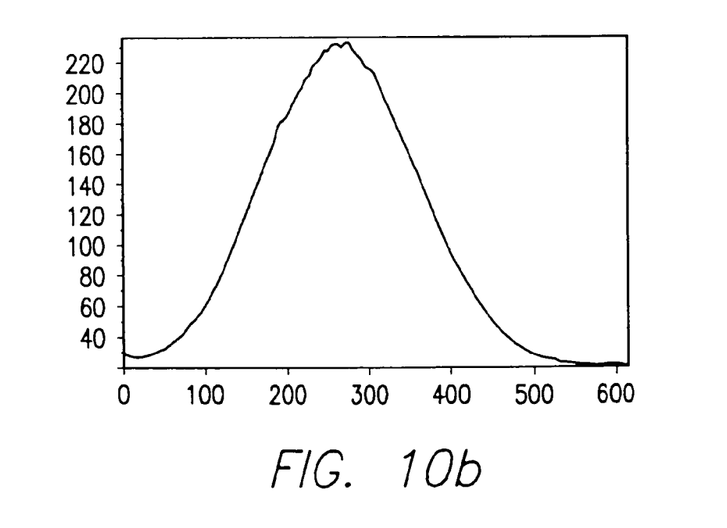

In another embodiment, photographic plates or films axe used in a conventional film projection type of system to project an irradiation pattern onto the IOL. As an example, FIG. 10b shows the beam profile of the 365 nm line from a mercury arc lamp after projection of the output of an optical fiber through an apodizing mask (FIG. 10a) possessing a $(1-r^2)$ optical density profile. Such intensity profile is used for irradiation of light adjustable lenses and produces desirable optical power changes in the lenses. According to this embodiment, each different intensity profile needs a new, individual mask to be placed in the projection system.

By using a liquid crystal display or a digital light processor to generate customized irradiation intensity profiles, the time and expense of making a customized photographic mask can be eliminated. Each customized irradiation intensity profile can be generated on a computer screen and then transferred to the liquid crystal display or digital light processor projector. The variable pattern on the computer screen can be produced with an equation representing a, 3-D image of the intensity pattern. The parameters of the equation can be varied by the doctor, using the patient's refraction and a nomogram. The physician can also make adjustments to the pattern/equation based on his/her own experience. In one embodiment, one can use the patient's refraction plus a wavefront analysis system to calculate the shape of the irradiation intensity profile for customized irradiation of the IOL.

As an example, the procedure in this embodiment generally involves making an incision in the anterior lens capsule to remove the cataractous crystalline lens and implanting a light adjustable lens in its place. After healing, the aberrations of the eye are measured either by conventional refraction techniques (defocus and astigmatism), by wavefront analysis (defocus, astigmatism, coma, spherical, and other higher order aberrations), and corneal topographical maps (for higher order aberrations). Knowledge of the aberrations as well as their spatial distribution in the eye after postsurgical healing then allows the patients vision to be corrected by a nomogram (representing the light adjustable lens' response to light of a particular wavelength, intensity profile, and duration) and the pattern generator to give optimal vision. After determination of the type, magnitude, and spatial distribution of the aberrations in the eye, this information is fed into a computer program that works in conjunction with the nomogram that outputs the correct intensity profile for the irradiating light source as well as the duration of the light. The required intensity profile is then fed into the digital light processor to control the individual mirrors that ultimately determine the output of the digital light processor projection system and the pattern is projected onto the light adjustable lens. Once the light adjustable lens is irradiated and diffusion of macromer to the exposed region has occurred the eye is again refracted. If further modification of the light adjustable lens is required the sequence of using the nomogram and the digital light processor pattern generator is repeated. Once the desired aberrations have been corrected, the entire lens is irradiated to photolock the lens, effectively prohibiting further diffusion and subsequent refraction changes in the light adjustable lens.

In another embodiment a digital light processor is used for the purpose of generating an irradiation profile/mask for UV irradiation of a light adjustable lens. A commercial digital light processor projector (such as sold by Infocus, Inc., can be purchased, the optics and light source can be removed, and replaced with a UV light source and lens system. The optics and light source can be replaced to irradiate test IOLs. Script can be generated for MatLab (commercial computer program for solving math problems and generating graphic images) or other graphics programs to view 3-D intensity profiles and 2-D intensity projections of those profiles. The computer can then be connected to the modified commercial projector and test IOLs can be irradiated with the calculated profiles. Flat disks and lenses can be made from the light adjustable lens material and irradiated with various patterns, intensity levels, and exposure times to generate one or more irradiation nomograms. Typical intensity patterns can resemble $(1-r^2)$ or Gaussian profiles (where r is the radius of the optical zone on the IOL). Typical intensity levels range from 2 to 10 mW/cm2 and typical exposure times range from 10 to 60 seconds. Patient's refraction data can be used with the nomogram for correcting the optical power and astigmatism in the IOL. For higher order aberrations, such as spherical aberrations and coma, a wavefront sensor will be required. Although more time consuming, standard refraction techniques have and can be used to measure spherical aberrations.

UV-VCSEL UV Pattern Generator

VCSELs can be single element lasers, 1-D arrays, or 2-d arrays. Each laser element emits a nearly square laser beam from the top surface in a narrow cone of light. Most of the research on these devices has been in the near IR for telecommunication applications. Some visible arrays have been developed for scanning and detecting images. The fill factor for 2-d arrays is usually small because of the space needed for the leads. Lens arrays can be placed on top of the VCSEL arrays to obtain fill factors greater than 90%. These lasers have very high modulation frequencies. If it is too difficult to control the intensity of the lasers, the energy in the exposure can be controlled with pulse width modulation or other modulation methods. By spatially controlling the intensity or average energy in each laser, one can produce an effective beam intensity profile. This pattern/profile is then imaged onto the light adjustable lens or film to produce the desired refraction pattern. The advantage is direct and instantaneous or nearly instantaneous control of the irradiation pattern and increased pattern combinations.

Since the same beam profile variation can be accomplished with various types of spatial light modulators and standard display or projection optics, the ramifications the UV-VCSEL of this embodiment are in the simplicity and size of the packaging issues are more important when the irradiation system is combined with the wavefront sensor and some type of viewing and video capability.

VCSELs have been used (at other wavelengths) in imaging and scanning applications but not for irradiating light adjustable lenses or films. Such UV-VCSEL arrays are as described in Photomiss Spectra, March 2001, p. 30, incorporated herein by reference.

Figure 11:
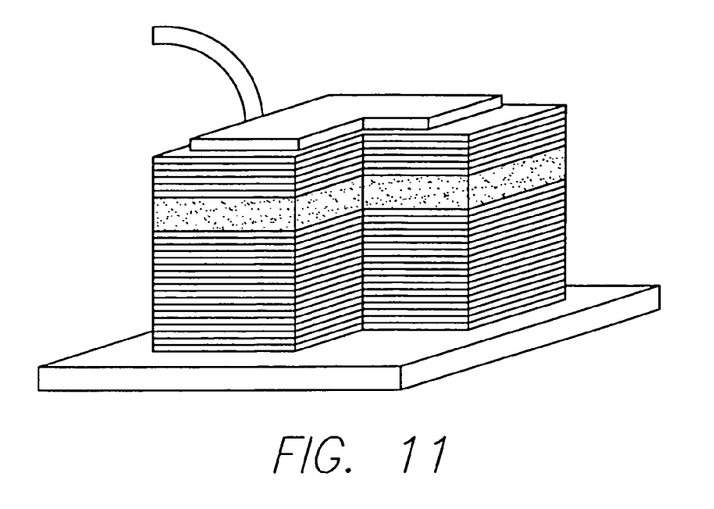
FIG. 11 is a schematic of a vertical cavity surface emitting laser usable in the present invention.

Referring to FIG. 11, in a VCSEL light propagates vertically rather than laterally through the structure. With this orientation the laser cavity can be grown to match the wavelength of laser light. With such a small cavity, the gain bandwidth of the device can only support a single longitudinal mode. In this particular VCSEL an oxide layer was grown directly above and below the laser cavity to provide both gain and index guiding to the device.

Gonio Lens to Lock Light Adjustable Lens

In accordance with an embodiment of this invention, a gognio lens is used to lock the light adjustable lens by irradiating portions of the light adjustable lens that are blocked by the iris. The advantage of this embodiment is that it can easily deliver radiation at large angles to reach portions of the lens that are behind the iris.

The gonio lens is typically a block of glass that has a radius on one end that matches the radius of curvature of the eye. A gel or viscoelastic material is used as an index matching fluid to remove or greatly reduce the optical power of the cornea. A lens on the other end allows one to look directly at the retina. Faceted mirrors are polished on the side of the block of glass that allows one to vie sides of the eye, either above or below the iris. Sometimes separate lenses are placed above the facets for focusing lasers inside the eye or aiding in the focus of other optical instruments. Since the areas of the eye are missed between the facets and where the facets come together, the gonio lens is rotated to provide complete coverage. The same missing areas will occur in this application of the gonio lens. Thus, the gonio lens will have to be rotated to provide complete coverage of the locking irradiation behind the iris.

Figure 12:
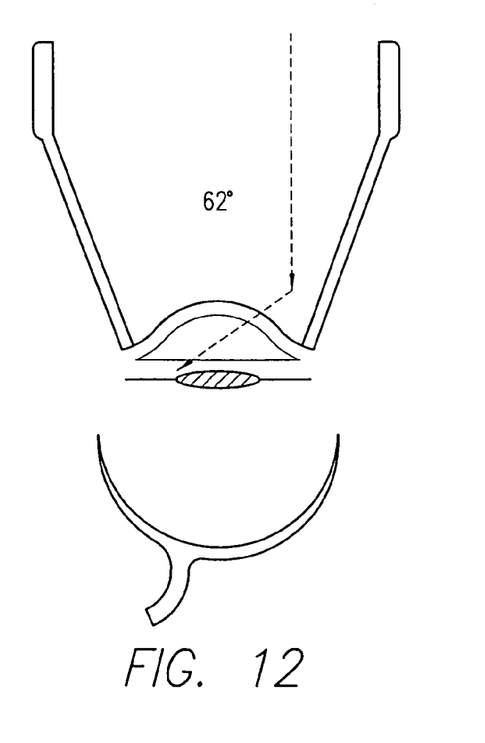
FIG. 12 is gonio lens usable in the present invention.
Figure 13:
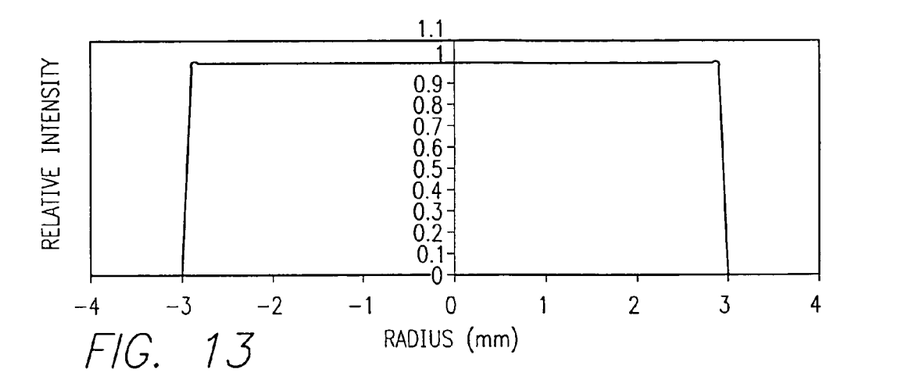
FIG. 13 is a nomogram used in this invention, having a "top hat" intensity profile.
Figure 14:
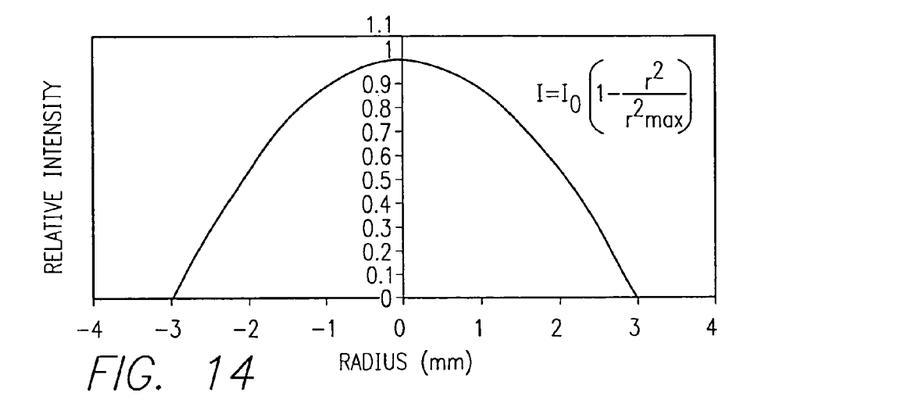
FIG. 14 is another nomogram used in this invention.
Figure 15:
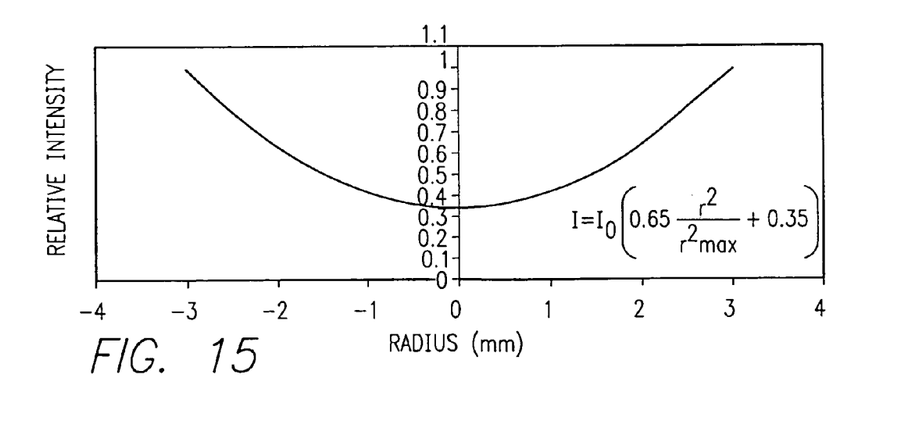
FIG. 15 is still another nomogram used in this invention, having a "hat" intensity profile.

Gonio lenses come with 1 to 4 facets. In this embodiment, a 4-mirror gonio lens is used because it gave the best coverage and required the least amount of rotation to obtain complete coverage. FIG. 12 illustrates a 4-mirror gonio lens, each mirror being at 62°. Four 62° millions give a 360° view, thereby a 360° projection of the anterior chamber angle with only a slight lens rotation. Such a gonio lens is available from Opt Electronics S. A. Medical Division Model 04GFA, or a Thorpe 4-mirror gonio laser lens Model OT4Mga. Other four mirror configurations can be used, such as the Ritch Trabeculopasty laser Lens Model ORTA, as well as single mirror or two mirror lenses. Examples are the Magic View Gonio laser lens Model OmVGL and the Single Mirror Gonio laser lens Model OSNGA, both having a single 62° mirror, and the two mirror gonio laser lens, Model O2MA having two opposing 62° mirrors. The gonio lens allows uniform rays from the irradiation source to get under the iris of the eye to the edges of the light adjustable lens, enabling total locking of the lens.

In General

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and/or steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. In a method for modifying the refractive power of a light adjustable lens in an optical system, with lens modifying radiation, the improvement comprising:
   aligning a source of the modifying radiation so as to impinge the radiation onto the lens in a pattern that corresponds to correct an aberration of the optical system; and
   controlling the quantity of the impinging radiation whereby to correct the aberration;
   wherein the impinging radiation is ultraviolet light obtained from a source thereof; and the ultraviolet light has a wavelength in the range of 350 to 380 nm and is applied at a power of 2.5 to 3.5 mW.

2. The method of claim 1 in which the quantity of the impinging radiation is controlled by controlling the intensity and duration of the irradiation.

3. The method of claim 1 in which the pattern of the impinging radiation is controlled and monitored while the lens is irradiated.

4. The method of claim 1 including the step of irradiating the entire lens to lock in the modified refractive power.

5. The method of claim 4 in which the modified refractive power of the light adjustable lens is locked in by non-patterned radiation.

6. The method of claim 1 in which the optical system comprises the light adjustable lens as an intraocular lens implanted in an eye.

7. The method of claim 1 in which the optical system comprises the light adjustable lens as a customized contact lens to be used in ophthalmic systems.

8. The method of claim 1 in which the optical system possesses at least one light adjustable refraction element that can be used to null the aberrations present in the system to improve image quality.

9. The method of claim 1 in which the ultraviolet light source comprises a plurality light emitting diodes whose outputs are directed onto the receiving end of a light pipe that directs the ultraviolet light onto the lens.

10. The method of claim 9 in which the light pipe is an optical fiber.

11. The method of claim 1 in which the ultraviolet light source comprises the output of a pulsed ultraviolet light laser.

12. The method of claim 1 in which the ultraviolet light is from a pulsed ultraviolet light laser.

13. The method of claim 1 in which the ultraviolet light source generates continuous wave ultraviolet light.

14. The method of claim 13 in which the continuous wave ultraviolet light is obtained from an arc lamp.

15. The method of claim 13 in which the continuous wave ultraviolet light is obtained from a continuous wave laser.

16. The method of claim 15 in which an ultraviolet vertical-cavity surface-emitting laser array is used to generate the pattern and project it onto the surface of the light adjustable lens.

17. The method of claim 15 in which the pattern is obtained by projecting ultraviolet light through an apodizing filter having a predetermined intensity profile.

18. The method of claim 15 in which the pattern is obtained by projecting ultraviolet light through a spatial light modulator.

19. The method of claim 18 in which the photo-feedback is obtained from a Shack-Hartmann sensor.

20. The method of claim 15 in which the pattern is obtained by reflecting ultraviolet light from a digital light processor.

21. The method of claim 15 in which the pattern is obtained by photo-feedback.

22. The method of claim 21 in which the non-patterned radiation has a "top hat" intensity profile.

23. The method of claim 21 in which the non-patterned radiation is has an intensity profile that diminishes as the radius increases.

24. The method of claim 21 wherein the optical system comprises the light adjustable lens as an intraocular lens implanted in an eye in which the iris does not fully dilate, and wherein the non-patterned radiation is projected through a gonio lens.

25. The method of claim 13 in which the continuous wave ultraviolet light is obtained from a continuous wave light emitting diode.

26. The method of claim 1 in which the ultraviolet light has a wavelength in the range of 350 to 380 nm and is applied at an intensity of 9.75 to 12.25 mW/cm$^2$.

27. The method of claim 26 in which the radius (r) increases by the formula: $(1 - r^2)/r^2$.

28. The method of claim 1 wherein the optical system is a component of a system selected from the group consisting of:

microscopes, telescopes, camera lenses, machine vision systems, video surveillance equipment, or satellite imaging equipment.

* * * * *